United States Patent
Tsui et al.

(10) Patent No.: US 9,412,167 B2
(45) Date of Patent: Aug. 9, 2016

(54) ACCELERATION AND ENHANCEMENT METHODS AND SYSTEM FOR ULTRASOUND SCATTERER STRUCTURE VISUALIZATION

(71) Applicant: AmCad BioMed Corporation, Taipei (TW)

(72) Inventors: Po-Hsiang Tsui, Tao-Yuan (TW); Ming-Chih Ho, Taipei (TW); Chiung-Nein Chen, Taipei (TW); Argon Chen, Taipei (TW); Jia-Jiun Chen, Taipei (TW); Yu-Hsin Wang, Taipei (TW); Kuo-Chen Huang, Taipei (TW)

(73) Assignee: AMCAD BIOMED CORPORATION, Taipei (TW)

( * ) Notice: Subject to any disclaimer, the term of this patent is extended or adjusted under 35 U.S.C. 154(b) by 0 days.

(21) Appl. No.: 14/704,257

(22) Filed: May 5, 2015

(65) Prior Publication Data
US 2016/0133020 A1    May 12, 2016

(30) Foreign Application Priority Data

Nov. 6, 2014    (TW) .............................. 103138518 A

(51) Int. Cl.
| | |
|---|---|
| G06K 9/00 | (2006.01) |
| G06T 7/00 | (2006.01) |
| A61B 8/14 | (2006.01) |
| A61B 8/00 | (2006.01) |

(52) U.S. Cl.
CPC ............. G06T 7/0034 (2013.01); A61B 8/14 (2013.01); A61B 8/461 (2013.01); G06T 7/0014 (2013.01); G06T 7/0026 (2013.01); G06T 2207/10132 (2013.01); G06T 2207/30024 (2013.01)

(58) Field of Classification Search
CPC combination set(s) only.
See application file for complete search history.

(56) References Cited

U.S. PATENT DOCUMENTS

| 4,783,839 A | * | 11/1988 | Bamber | .................. | G01S 7/412 348/163 |
| 5,566,674 A | * | 10/1996 | Weng | .................. | G01S 7/52046 600/443 |

(Continued)

OTHER PUBLICATIONS

Tsui et al., "Window-modulated compounding Nakagami imaging for ultrasound tissue characterization", Ultrasonics, May 6, 2014, pp. 1448-1459, vol. 54.

*Primary Examiner* — Anand Bhatnagar
(74) *Attorney, Agent, or Firm* — Muncy, Geissler, Olds & Lowe, P.C.

(57) ABSTRACT

The present invention provides an acceleration and enhancement methods for ultrasound scatterer structure visualization. The method includes: obtaining an ultrasonic image, calculating all values of the ultrasonic signal points in each $m^{th}$ window centered at a $n^{th}$ signal point to obtain a plurality of original statistical values $a_n x_m$, obtaining a plurality of $m^{th}$ statistical values by averaging value of original statistical values in the same window, calculating a plurality of $m^{th}$ weighting values based on the statistical values by different weighting formulas, multiplying each weighting value with the original statistical values corresponding to the various size of windows, summing up to obtain an ultrasound structure scatterer value of the $n^{th}$ ultrasonic signal point, and generating an ultrasound scatterer structure image based on a matrix of the ultrasound scatterer values. The present invention further combined interpolation method can reduce the computation time and retain the 80% accuracy.

14 Claims, 13 Drawing Sheets

(56) References Cited

U.S. PATENT DOCUMENTS

| | | | |
|---|---|---|---|
| 5,841,889 A * | 11/1998 | Seyed-Bolorforosh | G01S 7/52046 382/128 |
| 6,468,218 B1 * | 10/2002 | Chen | A61B 6/469 128/916 |
| 6,561,980 B1 * | 5/2003 | Gheng | A61B 8/12 600/443 |
| 7,273,455 B2 * | 9/2007 | Angelsen | G01S 7/52038 600/437 |
| 7,720,266 B2 * | 5/2010 | Ni | G01S 7/52034 378/37 |
| 7,811,233 B2 * | 10/2010 | Christopher | G01S 7/52038 600/443 |
| 2002/0133074 A1 * | 9/2002 | Chiao | G01S 7/52038 600/437 |
| 2010/0231909 A1 * | 9/2010 | Trainer | G01B 11/08 356/336 |
| 2015/0359512 A1 * | 12/2015 | Boctor | A61B 8/4263 600/444 |

* cited by examiner

US 9,412,167 B2

ACCELERATION AND ENHANCEMENT METHODS AND SYSTEM FOR ULTRASOUND SCATTERER STRUCTURE VISUALIZATION

FIELD OF THE INVENTION

The invention relates to a method and system for ultrasound scatterer structure visualization. In particular, the invention relates to an acceleration and enhancement method and system for ultrasound scatterer structure visualization.

BACKGROUND OF THE INVENTION

Conventional ultrasonic B-mode images qualitatively describe tissue structures but are unsuitable for quantitative analyses of scatterer properties. The scattering phenomenon is occurred when the incident wavelength is greater than the size of the scatterer in a tissue. The generated backscattered signals would form speckle, which exhibits a granular pattern of white and dark spots in the ultrasonic B-mode image. To avoid the influence of the speckle effect on the image quality, many methods were proposed to reduce the speckle appearance in the B-mode image. Nevertheless, due to that the backscattered signals are actually dependent on the shape, size, density, and other properties of the scatterers in a tissue, the information related to the scatterers carried by both the backscattered echoes and other weak signals might be lost in the B-mode image.

Several years ago, the Nakagami distribution, initially proposed to describe the statistics of the radar echoes, was applied to the statistical analysis of the ultrasonic backscattered signals. The Nakagami distribution has been shown to be a general model for all scattering conditions encountered in medical ultrasound by Shankar in 2000. However, it may be the possible causes of misdiagnosis from low image resolution when it is applied to characterize homogeneous tissues.

The primary object of the present invention is to provide an acceleration and enhancement method for ultrasound scatterer structure visualization to enhance image and characterize homogeneous tissues to avoid misdiagnosis.

SUMMARY OF THE INVENTION

The present invention relates to a method for ultrasound scatterer structure visualization. The present invention reflects the tissue characteristics and enhances the quality and the resolution of ultrasound scatterer structure images, in particular for homogeneous tissues. The present invention maintains the accuracy of the ultrasound scatterer structure images and avoids the computation time consumption by the interpolating method. The present invention is combined with the weighted average technique to accelerate and enhance the smoothness and the resolution of ultrasound scatterer structure images. The present invention also provides various clinical information to improve diagnostic accuracy.

The present invention provides a method for ultrasound scatterer structure visualization. The method for ultrasound scatterer structure visualization in accordance with the present invention comprises several steps. The method begins with obtaining an ultrasonic image signal including a plurality of ultrasonic signal points; each ultrasonic signal point comprises a value. Then, a plurality of values of the ultrasonic signal points in a first (sliding) window centered at a first ultrasonic signal point are calculated to obtain a first original statistical value $a_1 x_1$. A plurality of values of ultrasonic signal points in the first window centered at a second ultrasonic signal point are calculated to obtain a second original statistical value $a_2 x_1$, wherein an interval of one signal point between the first ultrasonic signal point and the second ultrasonic signal point. Following the rules as has been mentioned, a plurality of values of ultrasonic signal points in the first window centered at a $n^{th}$ ultrasonic signal point are calculated to obtain another original statistical values $a_n x_1$ until to obtain original statistical values for all ultrasonic signal points, wherein the interval of one signal point between two adjacent ultrasonic signal points. Then, a first statistical value based on an average of a total of the original statistical values $a_1 x_1$, $a_2 x_1$ ... $a_n x_1$ is calculated. Following the rules as has been mentioned, a second statistical value to a $m^{th}$ statistical value based on various size of windows are calculated. A first weighting value to a $m^{th}$ weighting value based on the statistical values is calculated, and they are used to obtain the weighted average of the ultrasonic backscattered statistical values. An ultrasound scatterer structure value of the first ultrasonic signal point is calculated by multiplying each weighting value with the original statistical values corresponding to the various size of windows and summing up. Following the rules as has been mentioned, the ultrasound scatterer values from the second ultrasonic signal point to the $n^{th}$ ultrasonic signal point are obtained. Finally, an ultrasound scatterer structure image is generated based on a matrix of the ultrasound scatterer values.

The present invention also provides a system for ultrasound scatterer structure visualization. The system for ultrasound scatterer structure visualization includes an ultrasound image capturing device, a processing unit and a display device. The ultrasound image capturing device obtains an ultrasonic image signal, wherein the ultrasonic image signal comprises a plurality of ultrasonic signal points; each ultrasonic signal point comprises a value. The processing unit electrically connected to the ultrasonic image capturing device is configured to calculate a plurality of values of the ultrasonic signal points in a first window centered at a first ultrasonic signal point to obtain a first original statistical value $a_1 x_1$; then a plurality of values of ultrasonic signal points in the first window centered at a second ultrasonic signal point are calculated to obtain a second original statistical value $a_2 x_1$, wherein an interval between the first ultrasonic signal point and the second ultrasonic signal point. A plurality of values of ultrasonic signal points in the first window centered at a $n^{th}$ ultrasonic signal point are calculated to obtain another original statistical values $a_n x_1$. The processing unit follows the mentioned rules until to obtain original statistical values for all ultrasonic signal points, wherein the interval between two adjacent ultrasonic signal points. The processing unit further calculates a first statistical value based on an average of the original statistical values $a_1 x_1$, $a_2 x_1$ ... $a_n x_1$. Following the rules as has been mentioned, a second statistical value to a $m^{th}$ statistical value based on various size of windows are calculated. The processing unit calculates a first weighting value to a $m^{th}$ weighting value based on the statistical values, and they are used to obtain the average of the ultrasonic backscattered statistical values. An ultrasound scatterer structure of the first ultrasonic signal point is calculated by multiplying each weighting value with the original statistical values corresponding to the various size of windows and summing up. Finally, the processing unit following the rules as has been mentioned, the ultrasound scatterer values from the second ultrasonic signal point to the $n^{th}$ ultrasonic signal point are obtained. A display device, electrically connects to the processing unit, is configured to generate an ultrasound scatterer structure image based on a matrix of the ultrasound scatterer values.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE INVENTION

The present invention discloses an acceleration and enhancement method for ultrasound scatterer structure visualization. It is understood that the method provides merely an example of the many different types of functional arrangements that may be employed to implement the operation of the various components of an ultrasound device, a computer system connected to the ultrasound device, a multiprocessor computing device, and so forth. The execution steps of the present invention may include application specific software which may store in any portion or component of the memory including, for example, random access memory (RAM), read-only memory (ROM), hard drive, solid-state drive, magneto optical (MO), IC chip, USB flash drive, memory card, optical disc such as compact disc (CD) or digital versatile disc (DVD), floppy disk, magnetic tape, or other memory components.

For embodiments, the computer system comprises a display device, a processing unit, a memory, an input device and a storage medium. The input device used to provide data such as image, text or control signals to an information processing system such as a computer or other information appliance. In accordance with some embodiments, the storage medium such as, by way of example and without limitation, a hard drive, an optical device or a remote database server coupled to a network, and stores software programs. The memory typically is the process in which information is encoded, stored, and retrieved etc. The processing unit performs data calculations, data comparisons, and data copying. The display device is an output device that visually conveys text, graphics, and video information. Information shown on the display device is called soft copy because the information exists electronically and is displayed for a temporary period of time. The display device includes CRT monitors, LCD monitors and displays, gas plasma monitors, and televisions. In accordance with such embodiments of present invention, the software programs are stored in the memory and executed by the processing unit when the computer system executes a method for ultrasound scatterer structure visualization. Finally, information provided by the processing unit, and presented on the display device or stored in the storage medium.

Figure 1:
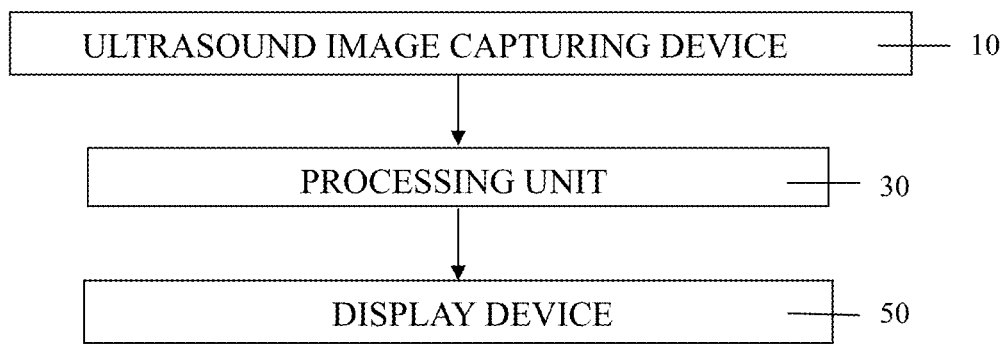
FIG. 1 a block diagram of a system for ultrasound scatterer structure visualization according to one embodiment of the invention.

FIG. 1 is a block diagram of an acceleration and enhancement system for ultrasound scatterer structure visualization in which embodiments of the ultrasonic image signal processing techniques disclosed herein may be implemented. As shown in FIG. 1, the acceleration and enhancement system for ultrasound scatterer structure visualization comprises an ultrasonic image capturing device 10, a processing unit 30 and a display device 50.

Figure 2:
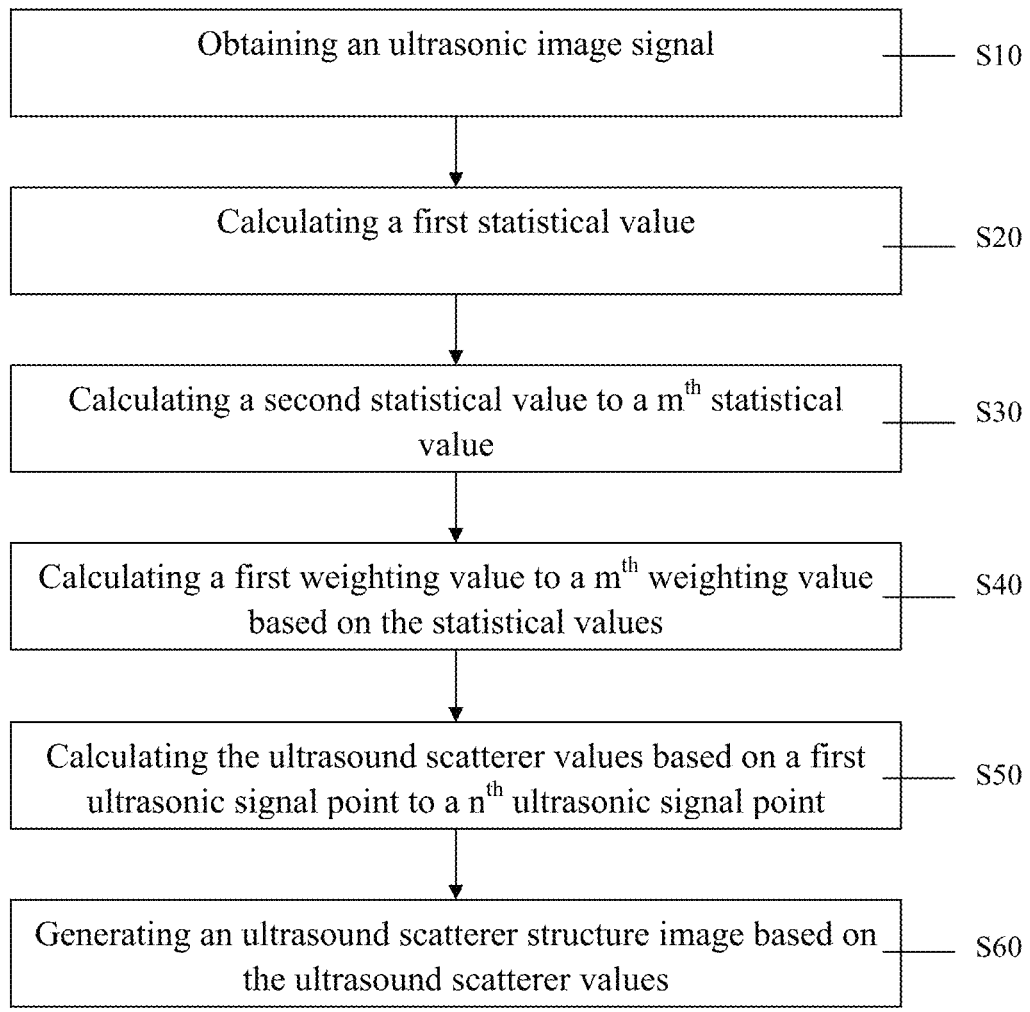
FIG. 2 is a flowchart of exemplary steps of a method for ultrasound scatterer structure visualization according to one embodiment of the invention.

Please refer FIG. 2; the ultrasonic image capturing device 10 may be an ultrasound probe for executing first step of the acceleration and enhancement method for ultrasound scatterer structure visualization to obtain an ultrasonic image signal (step S10). The system for ultrasound scatterer structure visualization obtains the ultrasonic image signal via the ultrasonic image capturing device 10. The ultrasonic image signal comprises a plurality of ultrasonic signal points (e.g., $a_1 \ldots a_n$), each ultrasonic signal point comprises a value. A matrix can be arranged by the plurality of ultrasonic signal points.

The processing unit 30 maybe a microprocessor or a processing unit of the computer system, electrically connected to the ultrasonic image capturing device 10 configured to calculate a first statistical value (step S20).

Figure 3:
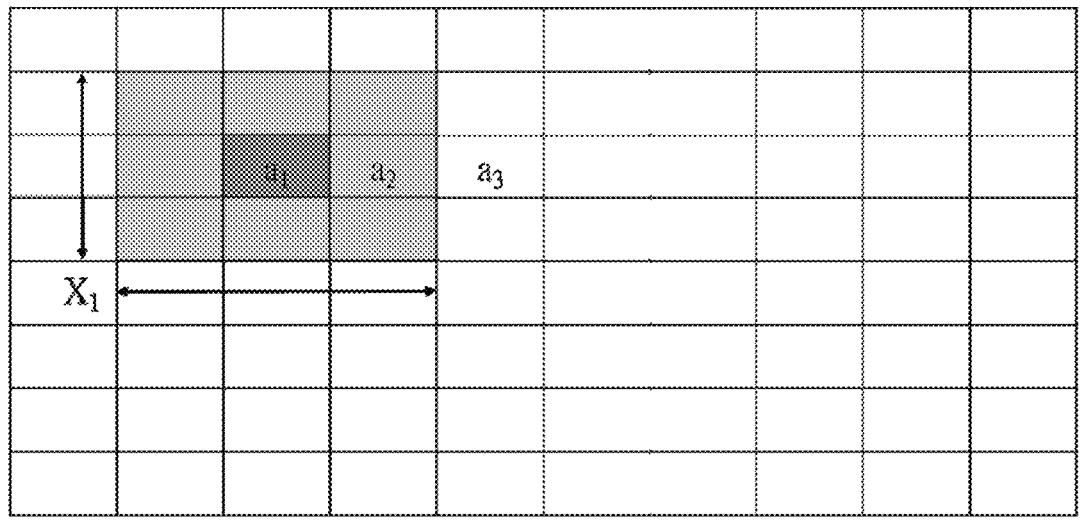
FIG. 3 illustrates a first ultrasonic signal point and a first window according to one embodiment of the invention.

Please refer FIG. 3, the details for S20 is described below. First, a first ultrasonic signal point $a_1$ is determined in a first window $x_1$. The values of all the ultrasonic signal points in the first window $x_1$ centered at the first ultrasonic signal point $a_1$ are calculated to obtain a first original statistical value $a_1x_1$. The first window $x_1$ such as a size of a quadrilateral window, so called a block. The quadrilateral window is suggested with a side length equal to a multiple of an incident pulse length. The gray-scale ultrasonic image is scanned begging from upper left corner. In the begging, the quadrilateral window is moving from a center point, for example, the first ultrasonic signal point $a_1$ to calculate the values of all the ultrasonic signal points in the first window $x_1$ to obtain the original statistical value $a_1x_1$. The first window $x_1$ comprises nine ultrasonic signal points; the original statistical values $a_1x_1$ is calculated based on the values of nine ultrasonic signal points ($a_1$ to $a_9$).

The original statistical value $a_1x_1$ is calculated based on different calculation methods for the values of all ultrasonic signal points, for example, calculating a mean, a standard deviation, a median, a mode or a percentile of all ultrasonic signal points.

For some embodiments, the original statistical value $a_1x_1$ reflects the statistical values for scatterer distribution within a tissue, such as the statistical values derived from the Nakagami model.

In accordance with one embodiment, the original statistical value $a_1x_1$ may be obtained by subtracting a mean of the values of all ultrasonic signal points in the window $x_1$ from a median of the values of all ultrasonic signal points in the window then dividing it by a standard deviation of the values of all ultrasonic signal points in the window $x_1$, as given by ((Median−mean)/std).

For one embodiment, the original statistical value $a_1x_1$ may be obtained by subtracting a 5th percentile of the values of all ultrasonic signal points in the window $x_1$ from a median of the values of all ultrasonic signal points in the window $x_1$, then dividing it with the subtraction between a 5th percentile of the values of all ultrasonic signal points in the window $x_1$ and a 95th percentile of the values of all ultrasonic signal points in the window $x_1$, as given by (Median−Percentile(5))/(Percentile(95)−Percentile(5)).

Figure 4:
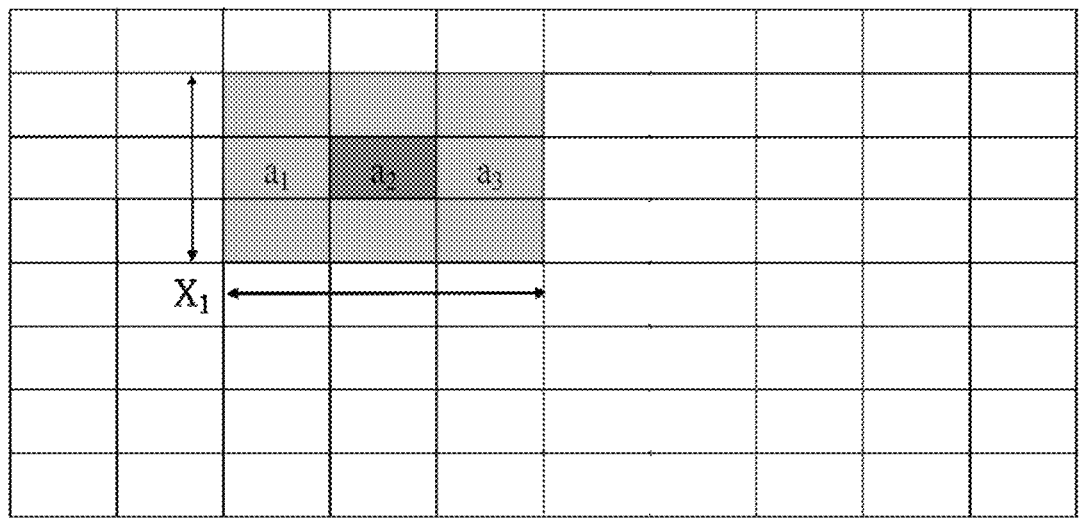
FIG. 4 illustrates a second ultrasonic signal point and a first window according to one embodiment of the invention.
Figure 5:
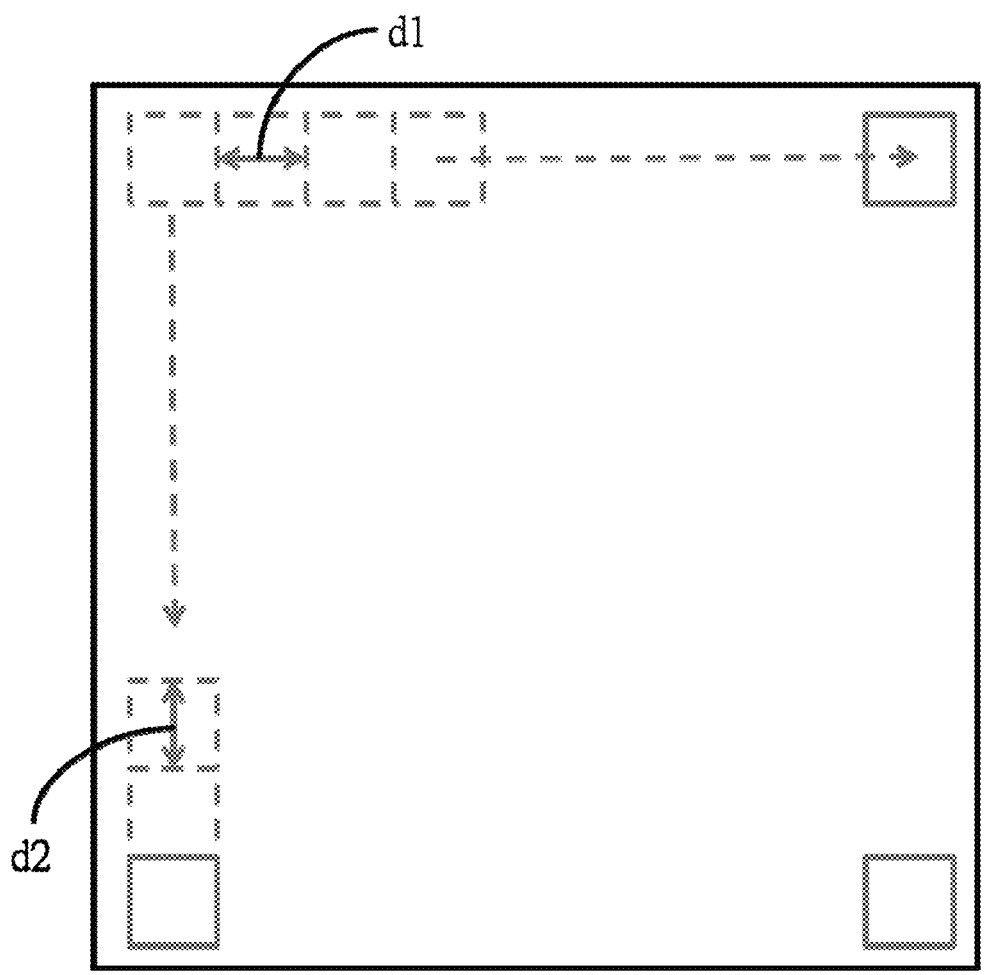
FIG. 5 illustrates a movement of the window according to one embodiment of the invention.

Please refer FIGS. 4 and 5, after the original statistical value $a_1x_1$ is calculated, the block is moving at a vertical distance $d_1$ or moving at a horizontal distance $d_2$ to a second ultrasonic signal point $a_2$. In FIG. 4, The distance between the first ultrasonic signal point $a_1$ and the second ultrasonic signal point $a_2$ may comprise one ultrasonic signal point. Furthermore, The values of all ultrasonic signal points in the first window $x_1$ centered at the second ultrasonic signal point $a_2$ are calculated to obtain a first original statistical value $a_2x_1$.

Accordingly, following the rules as has been mentioned, until all ultrasonic signal points in the whole ultrasonic image signal are calculated or scanned by the block to obtain a plurality of original statistical values $a_1x_1, a_2x_1, \ldots, a_{n-1}x_1$ for different center points with the same window. Finally, the values of all ultrasonic signal points in the first window $x_1$ centered at the $n^{th}$ ultrasonic signal point are used to calculate an original statistical value $a_nx_1$.

A first statistical value $w_1$ is calculated by summing and averaging of all original statistical values $a_1x_1, a_2x_1 \ldots a_nx_1$.

Figure 6:
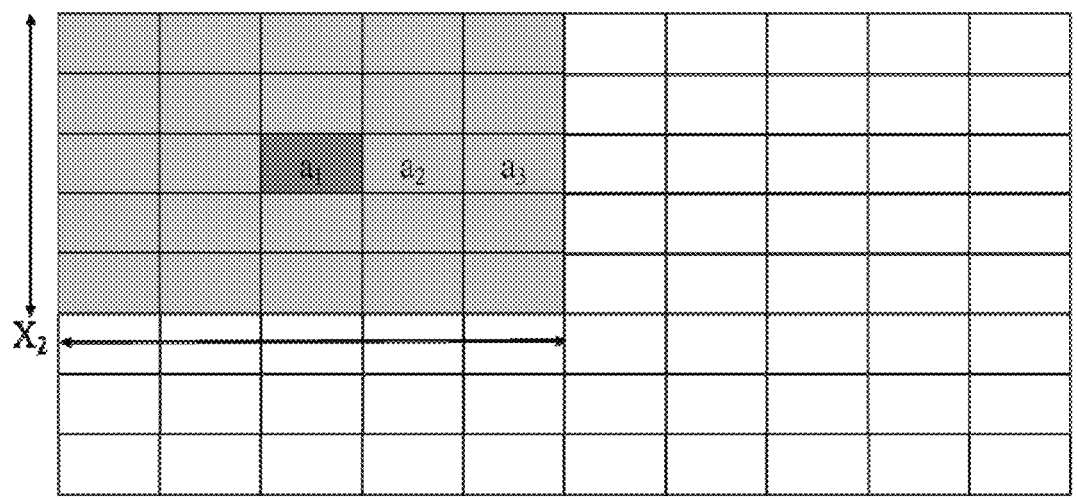
FIG. 6 illustrates a first ultrasonic signal point and a second window according to one embodiment of the invention.
Figure 7:
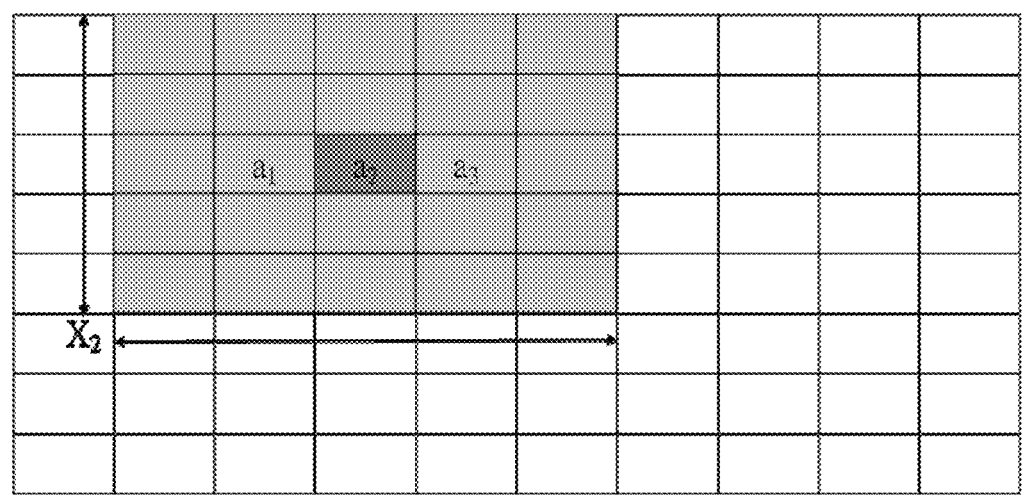
FIG. 7 illustrates a second ultrasonic signal point and a second window according to one embodiment of the invention.

The processing unit 30 calculates a second statistical value $w_2$ to the $n^{th}$ original statistical value $w_n$ (step S30). Following the rules as has been mentioned, the size of the block window x is adjusted. Please refer FIGS. 6 and 7, for example, scanning from upper left corner of the gray-scale ultrasonic image signal, the values of all ultrasonic signal points in the second window $x_2$ centered at the first ultrasonic signal point $a_1$ are used to calculate an original statistical value $a_1x_2$. Furthermore, the processing unit 30 obtains a plurality of original statistical values $a_2x_2, a_3x_2, \ldots a_nx_2$ with the second window $x_2$ centered at different the ultrasonic signal points, wherein the distance between two adjacent center points is one ultrasonic signal point.

Accordingly, following the rules as has been mentioned for calculating a first statistical value $w_1$ The processing unit 30 calculates a second statistical value $w_2$ by summing and averaging of the original statistical value $a_1x_2, a_2x_2 \ldots a_nx_2$ with the second window $x_2$. And so on, the size of the window x is adjusted to calculate the third statistical value $w_3$ to the $m^{th}$ statistical value $w_m$ with the third window $x_3$ to the $m^{th}$ window $x_m$.

Figure 8:
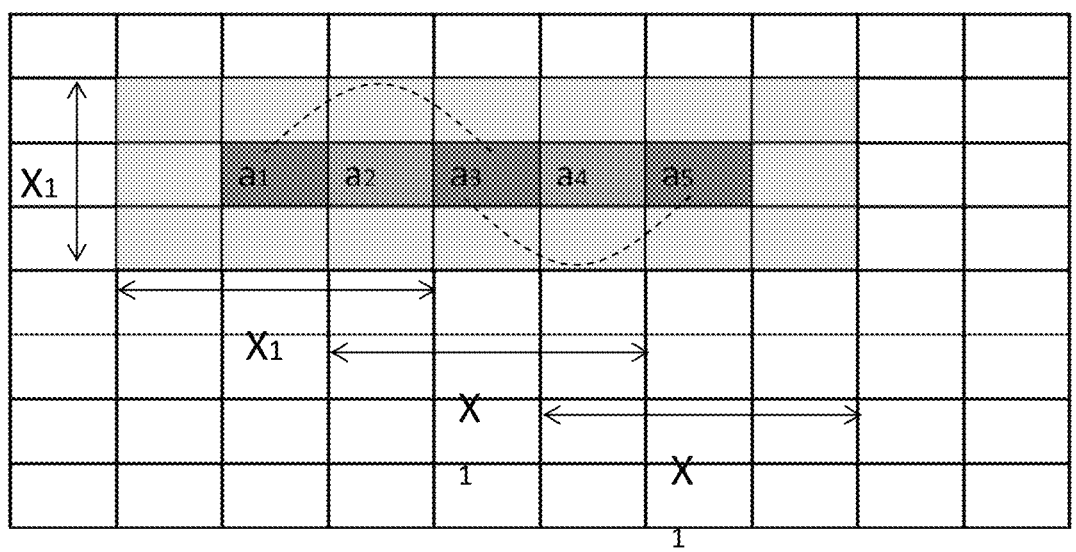
FIG. 8 illustrates an interpolation method according to one embodiment of the invention.

Please refer FIG. 8, for example, the vertical point distance d1 or horizontal point distance d2 can be an ultrasonic signal point. The present invention retains the 80% accuracy based on the results by the larger distance than one ultrasonic signal point. The processing unit 30 determines the distance between the points whether larger than one ultrasonic signal point. For example, in FIG. 8, when the point distance is two ultrasonic signal points, the processing unit 30 obtains the original statistical values $a_1x_1, a_3x_1$ and $a_5x_1$ centered at $a_1, a_3$ and $a_5$ first. Then, the original statistical values are calculated with an interpolating method to obtain a complete set of original statistical values. For example, the original statistical values $a_1x_1$ and $a_3x_1$ are used with the interpolating method to obtain an original statistical value $a_2x_1$, and the original statistical values $a_3x_1$ and $a_5x_1$ are used with the interpolating method to obtain the original statistical value $a_4x_1$. Therefore, the processing unit 30 only needs to determine half of the original statistical values and simply applies the interpolating method to obtain the complete set of original statistical values. The present invention does not need to calculate all original statistical values to avoid computation time consuming.

As discussed above, the processing unit 30 calculates a first weighting value $\alpha_1$ to a $m^{th}$ weighting value $\alpha_m$ based on the statistical values (step S40), wherein the values of $\alpha_1, \alpha_2 \ldots \alpha_m$ are weighting values for the original statistical values.

The processing unit 30 calculates an ultrasound scatterer structure value from the first ultrasonic signal point $a_1$ to the $n^{th}$ ultrasonic signal point $a_n$. Below is the detailed description, for the first ultrasonic signal point $a_1$, each weighting value $\alpha_1, \alpha_2, \ldots, \alpha_m$ multiplied by the original statistical values $a_1x_1, a_1x_2, \ldots, a_1x_m$ corresponding to the first ultrasonic signal point $a_1$ in the window. Finally, sum them up to obtain the ultrasound scatterer structure value for the first ultrasonic signal point $a_1$. The ultrasound scatterer structure value for the first ultrasonic signal point $a_1$ may be calculated according to the following expression:

$$\alpha_1 * a_1 x_1 + \alpha_2 * a_1 x_2 + \ldots + \alpha_m * a_1 x_m.$$

Accordingly, following the rules as has been mentioned for obtaining the ultrasound scatterer values for a second ultrasonic signal point $a_2$ to the $n^{th}$ ultrasonic signal, is expressed:

$$(\alpha_1 * a_2 x_1 + \alpha_2 * a_2 x_2 + \ldots + \alpha_m * a_2 x_m), (\alpha_1 * a_3 x_1 + \alpha_2 * a_3 x_2 + \ldots + \alpha_m * a_3 x_m) \ldots (\alpha_1 * a_n x_1 + \alpha_2 * a_n x_2 + \ldots + \alpha_m * a_n x_m)$$

The display device 50 electrically connected to the processing unit 30. The display device 50 such as, by way of example and without limitation, a computer monitor, a monitor for an ultrasound machine, a screen for mobile device, or other display device. The display device 50 represents an ultrasound scatterer structure image base on the ultrasound scatterer values (step S60). The ultrasound scatterer values can be represented by using conventional color gradient.

In accordance with such embodiments, the processing unit 30 performs different methods to calculate the weighting value for enhancement image resolution. For such embodiment, the processing unit 30 determines one of the statistical values $w_1, w_2 \ldots w_m$ for a reference value. The processing unit 30, for example, determines that the first statistical value $w_1$ is the reference value, and each statistical values $w_1, w_2, \ldots w_m$ divided by the reference vale to obtain a plurality of modulation statistical values $w_1', w_2' \ldots w_m'$. For example, the first, second, and third modulation statistical value may be calculated according to the following expressions respectively:

$$w_1' = w_1 / w_1, \; w_2' = w_2 / w_1, \; w_3' = w_3 / w_1,$$

and so forth. The weighting value $\alpha_1, \alpha_2 \ldots \alpha_m$ is calculated by the modulation statistical value divided by a total of the modulation statistical values. For example, the first, second, and third modulation statistical value may be calculated according to the following expressions respectively:

$$\alpha_1 = w_1' / (w_1' + w_2' + \ldots + w_m'), \; \alpha_2 = w_2' / (w_1' + w_2' + \ldots + w_m'), \; \alpha_3 = w_3' / (w_1' + w_2' + \ldots + w_m')$$

Figure 9:
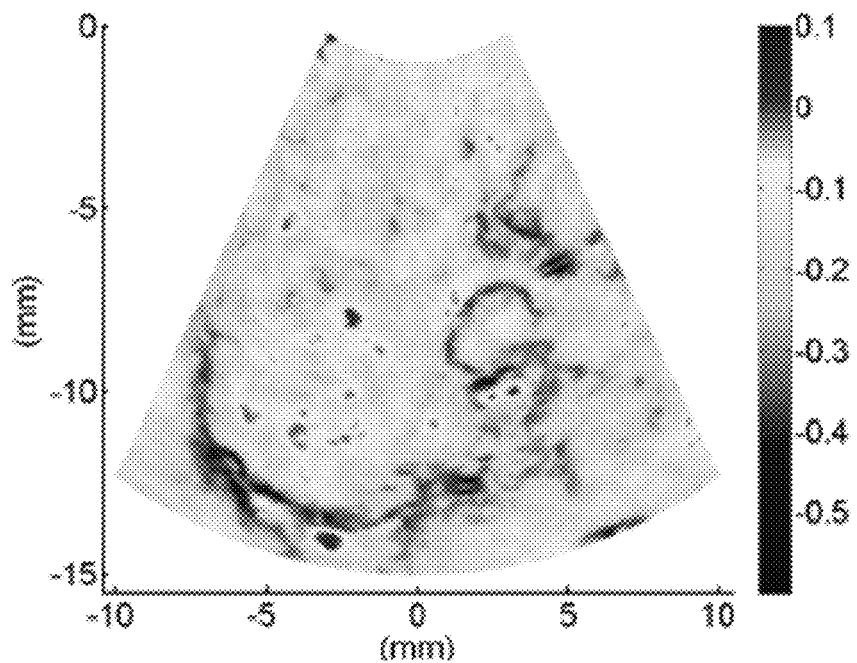
FIG. 9 illustrates an ultrasound scatterer structure image according to another embodiment of the invention when m=4.

As shown in the example of FIG. 9, for example, the statistical values are obtained by (Median−mean)/std, and the number of the windows is 4 (m=4). The comparison value $W_m$" is 0.709, 1.000, 0.844 and 0.743 in sequence. The processing unit 30 recalculates the ratios so that a total of weighting value is equal to one. Finally, the weighting value α is 0.2151, 0.3034, 0.2561 and 0.2254 in sequence.

In accordance with another embodiment, the processing unit 30 determines the weighting value α by performing a principle component analysis. A plurality of one-dimensional matrixes are arranged according to the statistical values $w_1$, $w_2 \ldots w_m$, then the weighting values $\alpha_1, \alpha_2, \ldots, \alpha_m$ are calculated based on the eigenvalue and the eigenvector. Please see more details below.

The plurality of one-dimensional matrixes are arranged according to the original statistical values, for example, ($a_1 x_1, a_2 x_1 \ldots a_n x_1$), ($a_1 x_2, a_2 x_2 \ldots a_n x_2$), ($a_1 x_3, a_2 x_3 \ldots a_n x_3$) ... ($a_1 x_m, a_2 x_m, \ldots a_n x_m$). In the expression:

$$\begin{bmatrix} I_{1,1} & I_{1,2} & \cdots & I_{1,g} \\ I_{2,1} & \ddots & & \vdots \\ \vdots & & \ddots & \vdots \\ I_{h,1} & \cdots & \cdots & I_{h,g} \end{bmatrix}$$

Wherein I represents the statistical values with different windows as a two-dimensional matrix (g points in width, h points in height). Two-dimensional matrix can be arranged into the one-dimensional matrix.

The processing unit 30 calculates a correlation coefficient matrix by subtracting an average value of the original statistical values from each original statistical value and dividing it with the standard deviation of the original statistical values. The correlation coefficient matrix represents the plurality of correlation coefficients from at least two one-dimensional matrixes according to the following expression:

$$\begin{bmatrix} 1 & C_{w1w2} & C_{w1w3} \\ C_{w2w1} & 1 & C_{w2w3} \\ C_{w3w1} & C_{w3w2} & 1 \end{bmatrix}$$

wherein $C_{w1w2}$ represents the correlation coefficients between the first group of original statistical values (for example, $a_1 x_1, a_2 x_1 \ldots a_n x_1$) in a one-dimensional matrix and the second group of original statistical values (for example, $a_1 x_2, a_2 x_2 \ldots a_n x_2$) in another one-dimensional matrix. The correlation coefficient may be calculated according to a formula, for example, the correlation coefficient of the first group of original statistical value matrix and the second group of original statistical value matrix according to the following expression:

$$\frac{n\sum_{i=1}^{n} x_i y_i - \sum_{i=1}^{n} x_i \sum_{i=1}^{n} y_i}{\sqrt{n\sum_{i=1}^{n} x_i^2 - \left(\sum_{i=1}^{n} x_i\right)^2} \sqrt{n\sum_{i=1}^{n} y_i^2 - \left(\sum_{i=1}^{n} y_i\right)^2}}$$

Where $x_i$ represents an element of the first group of original statistical value matrix, where $y_i$ represents an element of the second group of original statistical value matrix, and where i is from one to n, n represents the number of elements in the matrix.

The processing unit 30 calculates a maximum eigenvalue λ according to the correlation coefficient matrix. The maximum eigenvalue λ, may be calculated according to the following:

$$A - \lambda I_3 = \begin{bmatrix} 1 & C_{w1w2} & C_{w1w3} \\ C_{w2w1} & 1 & C_{w2w3} \\ C_{w3w1} & C_{w3w2} & 1 \end{bmatrix} - \lambda \begin{bmatrix} 1 & 0 & 0 \\ 0 & 1 & 0 \\ 0 & 0 & 1 \end{bmatrix} =$$

$$0 = \begin{bmatrix} 1-\lambda & C_{w1w2} & C_{w1w3} \\ C_{w2w1} & 1-\lambda & C_{w2w3} \\ C_{w3w1} & C_{w3w2} & 1-\lambda \end{bmatrix} = (1-\lambda)\begin{vmatrix} 1-\lambda & C_{w2w3} \\ C_{w3w2} & 1-\lambda \end{vmatrix} -$$

$$(C_{w1w2})\begin{vmatrix} C_{w2w1} & C_{w2w3} \\ C_{w3w1} & 1-\lambda \end{vmatrix} + (C_{w1w3})\begin{vmatrix} C_{w2w1} & 1-\lambda \\ C_{w3w1} & C_{w3w2} \end{vmatrix}$$

where λ is the maximum eigenvalue of A and A represents the correlation coefficient matrix.

The processing unit 30 calculates an eigenvector for the weighting value ($\alpha_m$) according to the maximum eigenvalue. The weighting values $\alpha_1$, $\alpha_2$ and $\alpha_3$ are calculated based on the maximum eigenvalue λ, the weighting value may be calculated according to the following:

$$\begin{bmatrix} 1-\lambda & C_{w1w2} & C_{w1w3} \\ C_{w2w1} & 1-\lambda & C_{w2w3} \\ C_{w3w1} & C_{w3w2} & 1-\lambda \end{bmatrix} \begin{bmatrix} \alpha_1 \\ \alpha_2 \\ \alpha_3 \end{bmatrix} = 0$$

Figure 10:
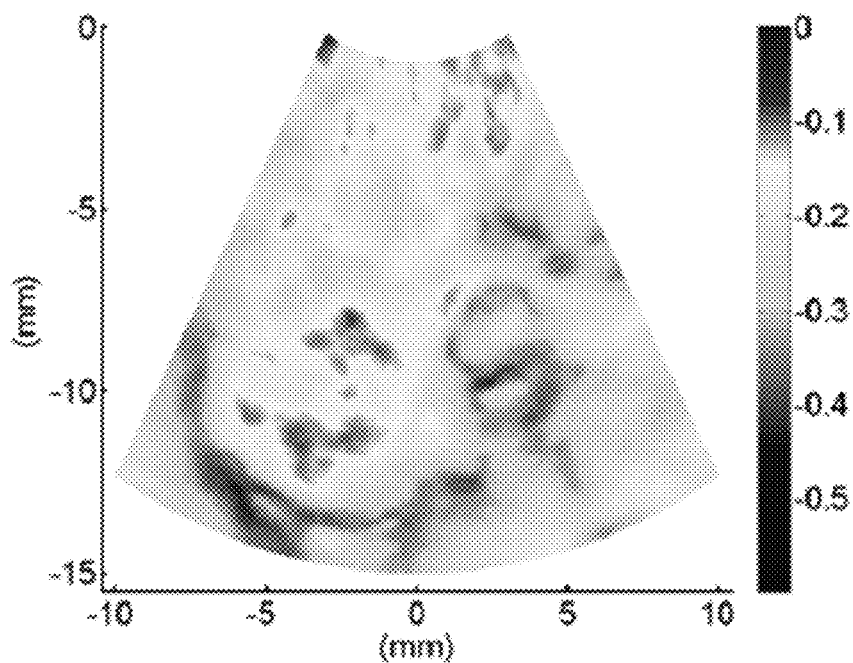
FIG. 10 illustrates an ultrasound scatterer structure image according to another embodiment of the invention when m=7.

As shown in the example in FIG. 10, the statistical values are calculated by (Median-mean)/std, and the number of the window is 7 (m=7). As described above, the maximum eigenvalue is calculated equal to 4.651, and the eigenvector is [0.1269, 0.3269, 0.4123, 0.4373, 0.4352, 0.4025 0.4054]. The ratios are recalculated so that a total of weighting value is equal to one. Finally, the weighting values are 0.0498, 0.1284, 0.1619, 0.1717, 0.1709, 0.1581 and 0.1592, as shown in FIG. 10.

Figure 11:
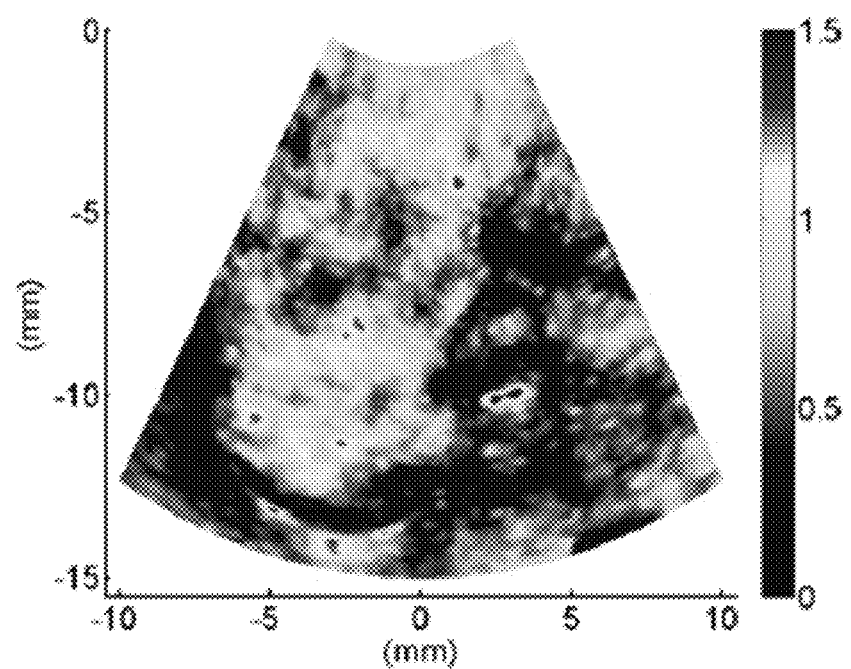
FIG. 11 illustrates an ultrasound scatterer structure image according to another embodiment of the invention when m=7.

As shown in the example in FIG. 11, the m blocks with various sizes are inputted by the user. The statistical values are calculated with the different windows, and the weighting values $\alpha_1, \alpha_2 \ldots \alpha_m$ are the reciprocal of the number of the windows (m). The weighting value is calculated according to the following expression:

$$\alpha_1 = \alpha_2 = \ldots = \alpha_m = 1/m$$

The ultrasound scatterer structure value of a first ultrasonic signal point $a_1$ is calculated according to the following expression:

$$(1/m * a_1 x_1 + 1/m * a_1 x_2 + \ldots + 1/m * a_1 x_m)$$

Following the rules as has been mentioned, the ultrasound scatterer structure value of the second ultrasonic signal pint $a_2$ to the $n^{th}$ ultrasonic signal pint $a_n$ are calculated according to the following expression:

$$(1/m*a_2 x_1 + 1/m*a_2 x_2 + \ldots + 1/m*a_2 x_m), (1/m*a_3 x_1 + 1/m*a_3 x_2 + \ldots + 1/m*a_3 x_m) \ldots (1/m*a_n x_1 + 1/m*a_n x_2 + \ldots + 1/m*a_n x_m)$$

This method is called window-modulated Compounding. As shown in FIG. 11, which illustrates an example of an ultrasound scatterer statistical image based on the ultrasound scatterer signal, and the statistical values are derived from the Nakagami model and the number of the windows is 7 (m=7).

To present a conclusion about the impact of distance of ultrasonic signal point on acceleration of ultrasound scatterer structure visualization and quality of ultrasound scatterer structure visualization. For one embodiment, four different distances for the block movement are predetermined; for example, an window overlapping rate is larger than 95% (over 95), an window overlapping rate is 75% (over 75), an window overlapping rate is 50% (over 50), and an window overlapping rate is 25% (over 25). The window overlapping rate with a lower value represents a larger amount of movement distance.

For example, a block (12×72) is determined as the double of transmitted pulse length. As described above, the window overlapping rate is larger than 95% (over 95) when the block is moving at one ultrasound signal point both in horizontal and vertical. The window overlapping rate is 75% when the block is moving at three ultrasonic image signal points in horizontal and at eighteen ultrasonic image signal points in vertical. The window overlapping rate is 50% when the block is moving at six ultrasonic image signal points in horizontal and at thirty six ultrasonic image signal points in vertical. The window overlapping rate is 25% when the block is moving at nine ultrasonic signal points in horizontal and at fifty four ultrasonic signal points in vertical.

Figure 12A:
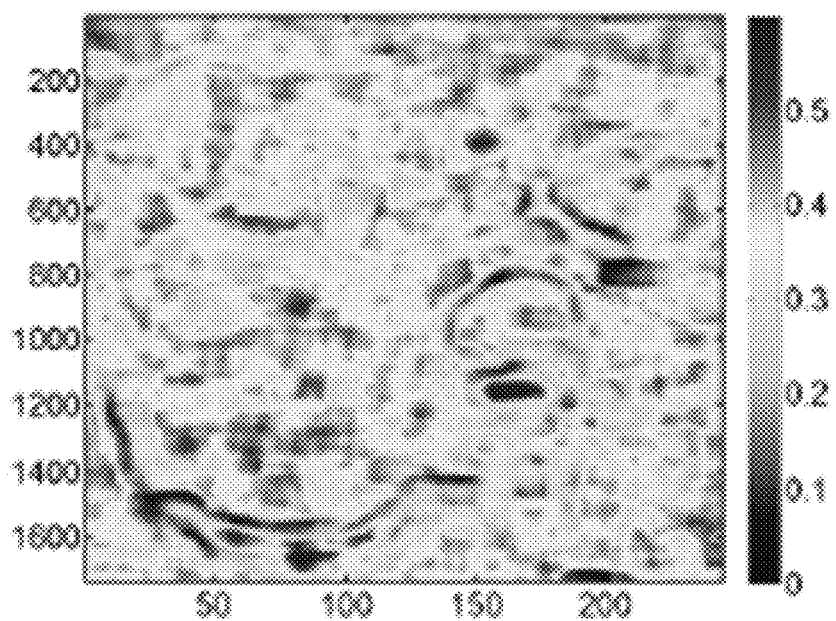
FIGS. 12a to 12d illustrate an ultrasound scatterer structure image with different window overlapping rates according to one embodiment of the invention.

FIGS. 12a to 12j illustrate ultrasound scatterer structure images based on the statistical values when the window overlapping rate is larger than 95%, equal to 75%, equal to 50% or equal to 25%. FIG. 12a illustrates the matrix (244×1739) of the statistical values of the ultrasonic signal point. FIGS. 12b to 12j illustrates ultrasound scatterer structure images based on the lower window overlapping rate. However, the computation efficiency is improved compared to FIG. 12a and the matrix size of the statistical vales is smaller than FIG. 12a.

The complete matrix of the statistical value is obtained with the interpolation method and its size is equal to that of FIG. 12a (window overlapping rate larger than 95%). The complete matrix of the statistical value can be represented by using conventional color gradient to display the image.

Figure 12B:
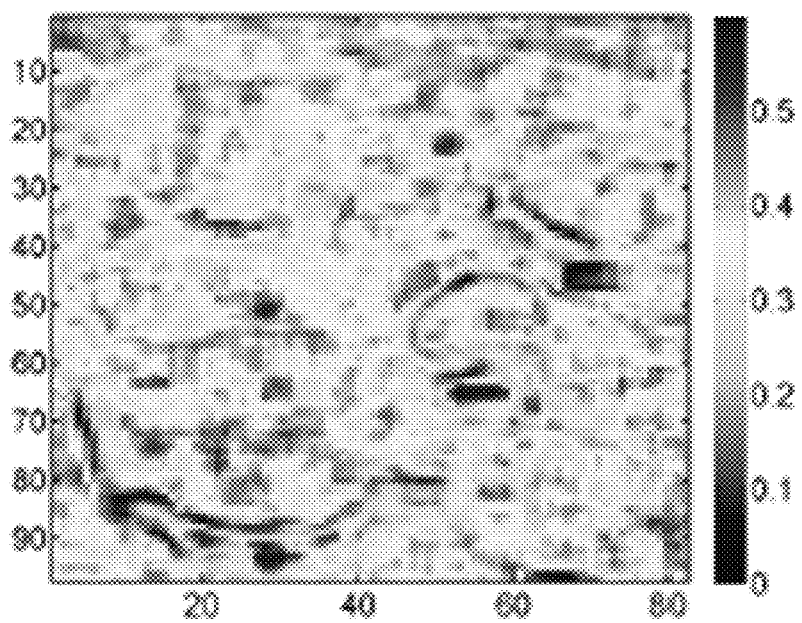
Figure 12C:
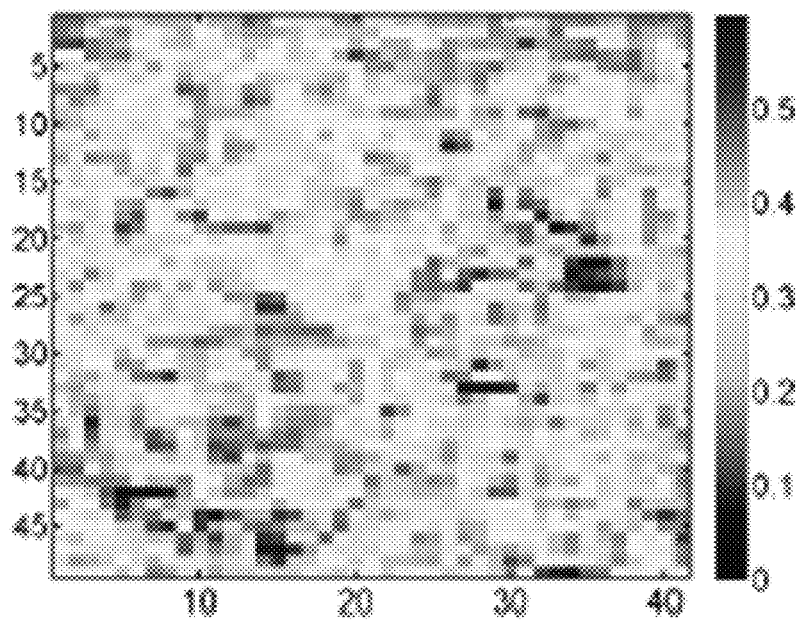
Figure 12D:
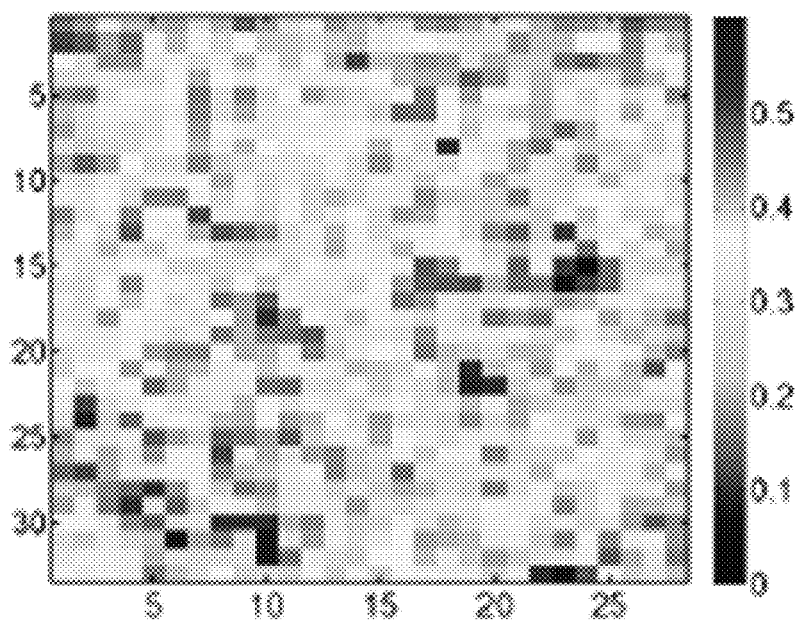
Figure 12E:
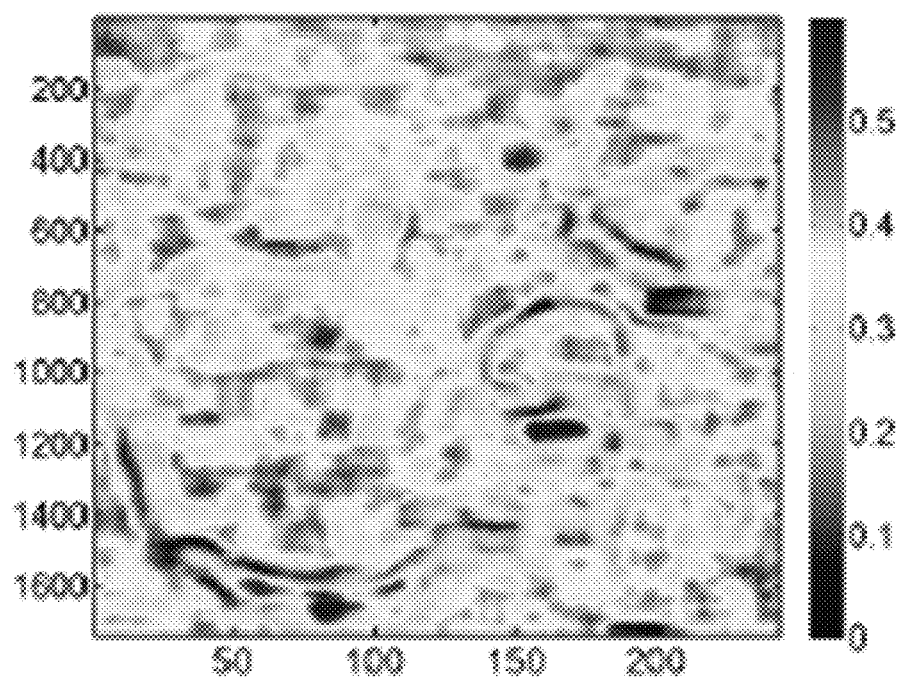
FIGS. 12e to 12g illustrate an ultrasound scatterer structure image based on the statistical values, with different window overlapping rates, combined an interpolation method according to one embodiment of the invention.
Figure 12F:
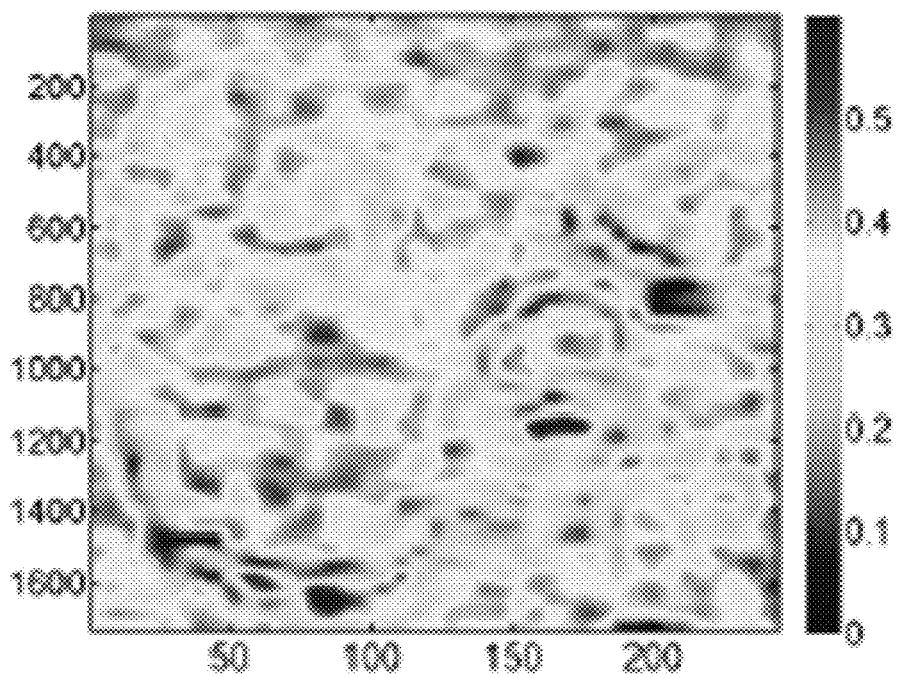
Figure 12G:
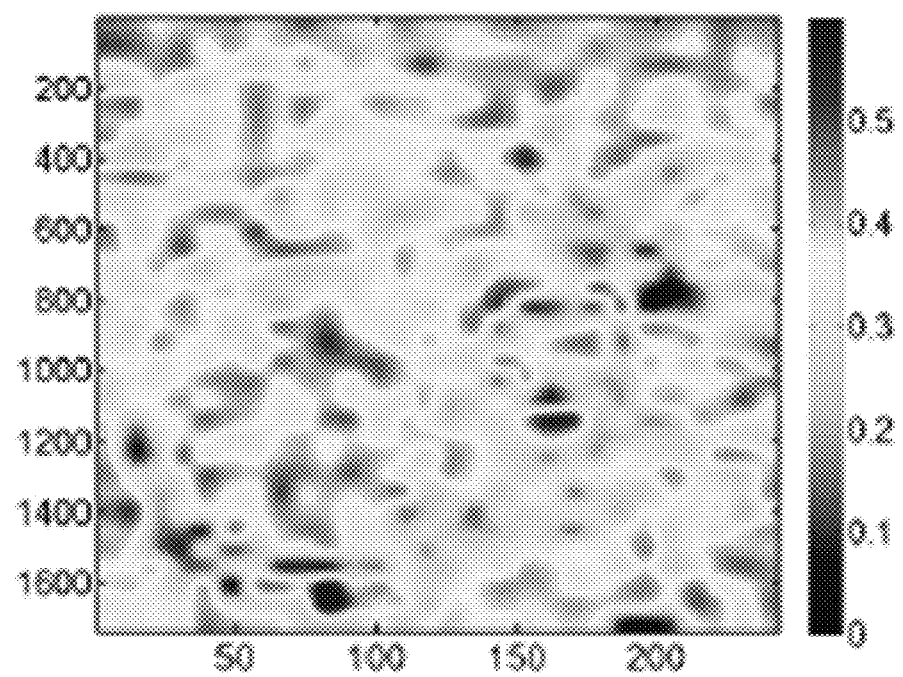
Figure 12H:
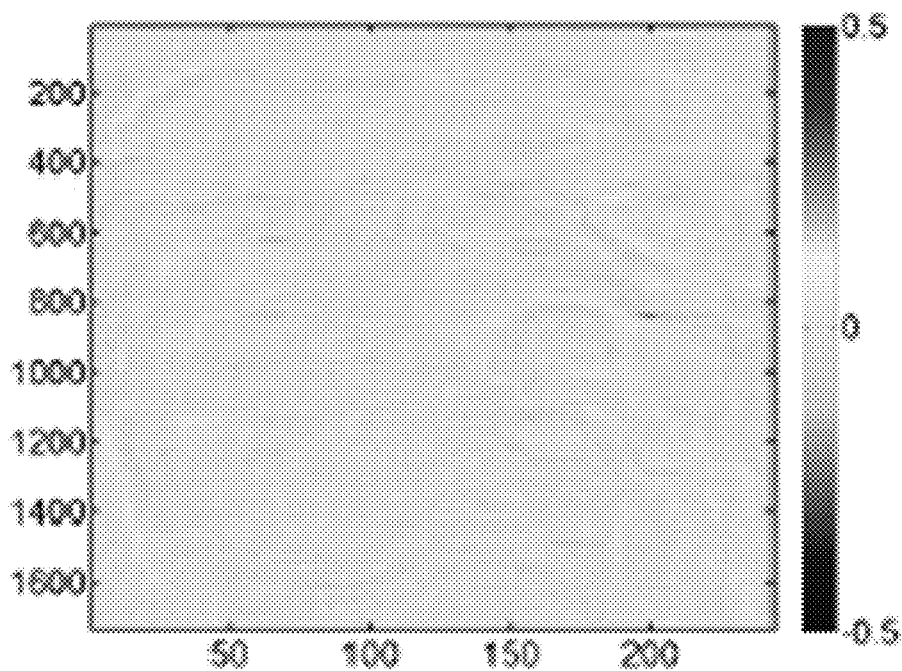
FIG. 12h to FIG. 12j depict the examples of the ultrasound scatterer structure image based on the subtraction of statistical values between FIG. 12e and FIG. 12a, FIGS. 12f and 12a, FIGS. 12g and 12a respectively.
Figure 12I:
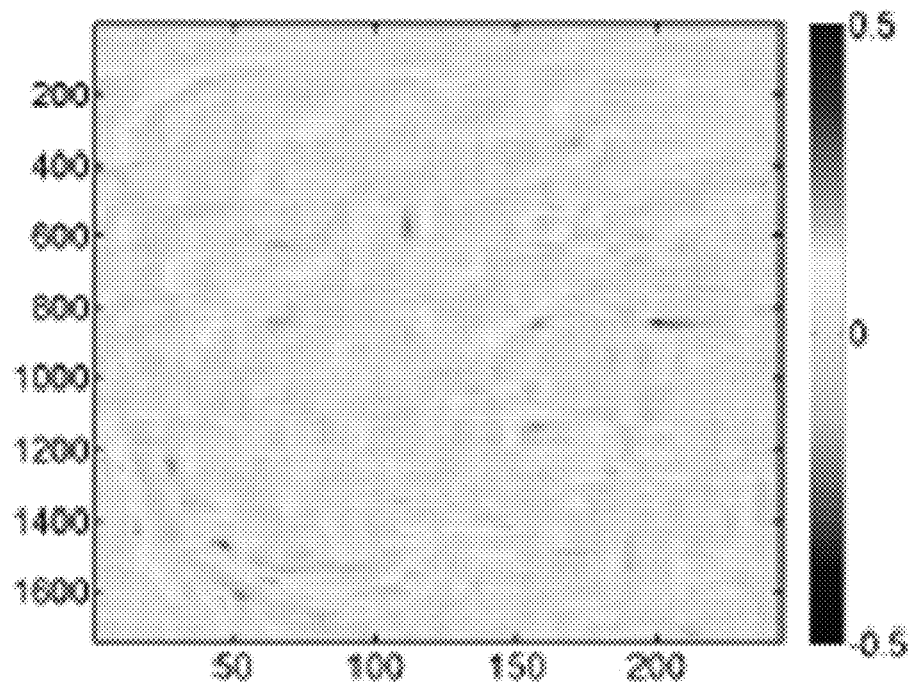
Figure 12J:
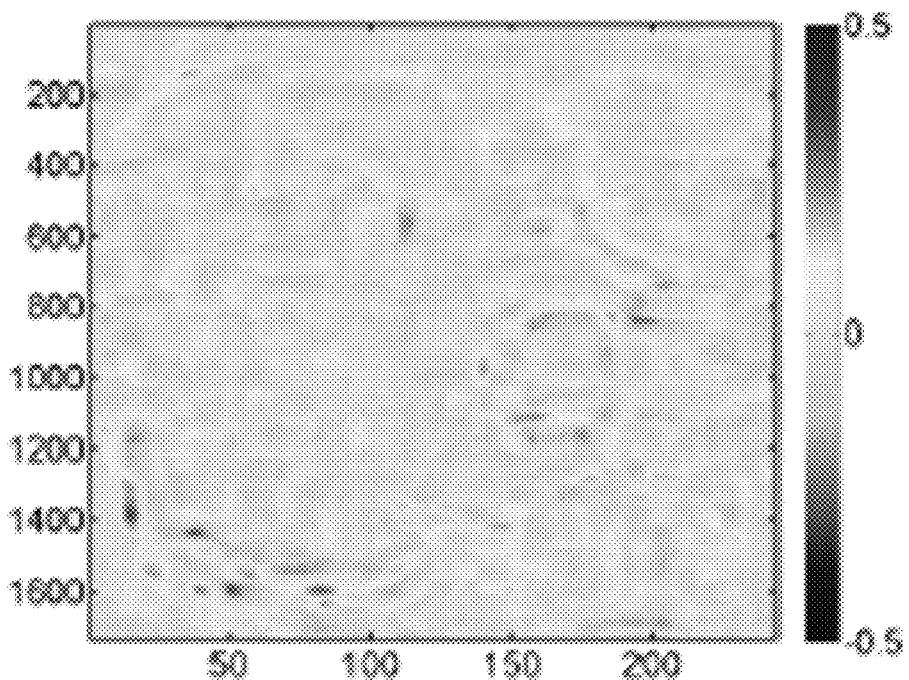

As shown in FIG. 12e to FIG. 12g, the complete matrixes of the statistical values in FIG. 12b to FIG. 12d are obtained with the interpolation method and the matrix size is equal to that of FIG. 12a. In FIG. 12a, the block is moving at one ultrasonic image signal point both in vertical and horizontal to obtain best tissue characterization, so FIG. 12a is used as reference. As shown in FIGS. 12h to 12j, subtract the corresponding ultrasonic signal point value in FIG. 12a from each ultrasonic signal point value in FIGS. 12e to 12g to obtain the error rates, which are 5.04%, 8.76% and 11.31%. The table 1 illustrates the computation time; therefore the present invention provides a method reduces the computation time and retains the 80% accuracy.

TABLE 1

The computation time and error rates with different window overlapping rates.

| window overlapping rate | >95% | 75% | 50% | 25% |
|---|---|---|---|---|
| computation time (sec) | 40.74 | 0.98 | 0.41 | 0.31 |
| error rate (%) | — | 4.016 | 7.284 | 9.95 |

As described above, the present invention provides three methods to illustrate the image resolution enhancement based on the smoothness of amplitudes between ultrasound statistical values.

The present invention provides an acceleration and enhancement method and system for ultrasound scatterer structure visualization and facilitates to evaluate distribution of scatterers and structure, for example, in the internal of the liver. The object of the present invention is combined with the weighted average technique to accelerate and enhance the smoothness and the resolution of the ultrasonic image, to improve the quality of the ultrasonic image, and to characterize homogeneous tissues. Furthermore, as a fixed distance for the block movement is more than one ultrasonic signal points, simply apply the interpolating method to obtain the complete set of original statistical value for maintaining the accuracy of operation and avoiding computation time consuming. The present invention provides variously practical clinical information to improve diagnostic accuracy. The algorithms are given to calculate the various types of weighting values that provide medical professionals with more options for diagnosis and to improve the quality of the ultrasonic image and to characterize homogeneous tissues.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A method for ultrasound scatterer structure visualization, comprising:

obtaining an ultrasonic image signal, wherein the ultrasonic image signal comprises a plurality of ultrasonic signal points, each ultrasonic signal point comprises a value;

defining a first window, wherein a central point of the first window is a first ultrasonic signal point; calculating a plurality of values of the ultrasonic signal points in the first window to obtain a first original statistical value $a_1x_1$;

moving the central point of the first window to a second ultrasonic signal point, calculating a plurality of values of ultrasonic signal points in the first window to obtain a second original statistical value $a_2x_1$, wherein an interval between the first ultrasonic signal point and the second ultrasonic signal point is one signal point;

calculating a plurality of values of ultrasonic signal points in the first window centered at different ultrasonic signal points, obtaining a $n^{th}$ original statistical value $a_nx_1$ until the first window is moving throughout all ultrasonic signal points, wherein the interval between two adjacent ultrasonic signal points is one signal point;

calculating a first statistical value by averaging the original statistical value s $a_1x_1, a_2x_1 \ldots a_nx_1$;

calculating a second statistical value to a $m^{th}$ statistical value based on various size of the windows;

calculating a first weighting value to a $m^{th}$ weighting value based on the plurality of statistical values;

calculating an ultrasound scatterer structure value of the first ultrasonic signal point based on multiplying each weighting value with the original statistical values corresponding to the various size of windows, and summing up;

calculating the plurality of ultrasound scatterer structure values from the second ultrasonic signal point to the $n^{th}$ ultrasonic signal point; and generating an ultrasound scatterer structure image based on a matrix of the ultrasound scatterer structure values.

2. The method of claim 1, wherein calculating the original statistical values for all ultrasonic signal points further comprises:

calculating the original statistical values through applying an interpolating method when the interval between two ultrasonic signal points is more than one signal points.

3. The method of claim 1, wherein the first weighting value to the $m^{th}$ weighting value are a reciprocal of the number of windows.

4. The method of claim 1, wherein calculating the weighting values further comprises:
calculating a plurality of comparison values based on the ratio of statistical values to a reference value, wherein the reference value is one of the statistical values, and the first weighting value to the $m^{th}$ weighting value are obtained by each comparison value divided by a sum of the plurality of comparison values.

5. The method of claim 1, wherein calculating the weighting values further comprises:
calculating a plurality of comparison values based on the ratio of statistical values to the reference value, when the comparison value is higher than one, subtracting comparison value from two to get a new comparison value, when the comparison value less than or equal to one, the comparison value remains the same; wherein the first weighting value to the $m^{th}$ weighting value are obtained by each comparison value divided by the sum of the plurality of comparison values.

6. The method of claim 1, wherein calculating the weighting values further comprises:
calculating a eigenvector based on a eigenvalue of the original statistical values derived from various size of windows, wherein the first weighting value to the $m^{th}$ weighting value are individually corresponding to the elements of eigenvector.

7. The method of claim 6, wherein calculating the eigenvalue and the eigenvector comprises:
arranging a plurality of one-dimensional matrixes according to the original statistical values corresponding to the statistical values;
subtracting an average value of the original statistical values from each original statistical value, then dividing by a standard deviation of the original statistical values;
obtaining a correlation coefficient matrix, wherein the correlation coefficient matrix comprises the plurality of correlation coefficients from any two one-dimensional matrixes;
calculating a maximum eigenvalue based on the correlation coefficient matrix; and
calculating the eigenvector for the weighting values based on the maximum eigenvalue.

8. A system for ultrasound scatterer structure visualization, comprising:
an ultrasound image capturing device configured to obtain an ultrasonic image signal, wherein the ultrasonic image signal comprises a plurality of ultrasonic signal points, each ultrasonic signal point comprises a value;
a processing unit electrically connected to the ultrasound image capturing device configured to:
calculate a plurality of values of the ultrasonic signal points in a first window to obtain a first original statistical value $a_1x_1$, wherein a central point of the first window is a first ultrasonic signal point;
move the central point of the first window to a second ultrasonic signal point, calculate a plurality of values of ultrasonic signal points in the first window to obtain a second original statistical value $a_2x_1$, wherein an interval between the first ultrasonic signal point and the second ultrasonic signal point is one signal point;
calculate a plurality of values of ultrasonic signal points in the first window centered at different ultrasonic signal points, then obtain a $n^{th}$ original statistical value $a_nx_1$ until the first window is moving throughout all ultrasonic signal points, wherein the interval between two adjacent ultrasonic signal points is one signal point;
calculate a first statistical value by averaging the original statistical values $a_1x_1, a_2x_1, \ldots a_nx_1$;
calculate a second statistical value to a $m^{th}$ statistical value based on various size of the windows;
calculate a first weighting value to a $m^{th}$ weighting value based on the plurality of statistical values;
calculate an ultrasound scatterer structure value of the first ultrasonic signal point based on multiplying each weighting value with the original statistical values corresponding to the various size of windows, and summing up; and
calculate the plurality of ultrasound scatterer structure values from the second ultrasonic signal point to the $n^{th}$ ultrasonic signal point; and
a display device electrically connected to the process device configured to generate an ultrasound scatterer structure image based on a matrix of the ultrasound scatterer values.

9. The system of claim 8, wherein the processing unit calculates the original statistical values for all ultrasonic signal points further configured to calculate the original statistical values through applying an interpolating method when the interval between two ultrasonic signal points is more than one signal points.

10. The system of claim 8, wherein the first weighting value to the $m^{th}$ weighting value are a reciprocal of the number of windows.

11. The system of claim 8, wherein the processing unit further configured to calculate a plurality of comparison values based on the ratio of statistical values to a reference value, wherein the reference value is one of the statistical values, and the first weighting value to the $m^{th}$ weighting value are obtained by each comparison value divided by a sum of the plurality of the comparison values.

12. The system of claim 8, wherein the processing unit further configured to calculate a plurality of comparison values based on the ratio of statistical values to the reference value, when the comparison value is higher than one, subtracting comparison value from two to get a new comparison value, when the comparison value less than or equal to one, the comparison value remains the same; wherein the first weighting value to the $m^{th}$ weighting value are obtained by each comparison value divided by the sum of the plurality of comparison values.

13. The system of claim 8, wherein the processing unit further configured to calculate a eigenvector based on a eigenvalue of the original statistical values derived from various size of windows, wherein the first weighting value to the $m^{th}$ weighting value are individually corresponding to the elements of eigenvector.

14. The system of claim 8, wherein the processing unit is further configured to calculate the eigenvalue and the eigenvector to:
arrange a plurality one-dimensional matrixes according to the original statistical values corresponding to the statistical values;
subtract an average value of the original statistical values from each original statistical value, then dividing by a standard deviation of the original statistical values;

obtain a correlation coefficient matrix, wherein the correlation coefficient matrix comprises the plurality of correlation coefficients from any two one-dimensional matrixes;

calculate a maximum eigenvalue based on the correlation coefficient matrix; and calculate the eigenvector for the weighting values based on the maximum eigenvalue.

* * * * *